United States Patent [19]

Hopkins

[11] Patent Number: 4,559,307
[45] Date of Patent: Dec. 17, 1985

[54] TREATMENT OF YEAST CELLS WITH PROTEOLYTIC ENZYMES

[75] Inventor: Thomas R. Hopkins, Bartlesville, Okla.

[73] Assignee: Phillips Petroleum Company, Bartlesville, Okla.

[21] Appl. No.: 542,846

[22] Filed: Oct. 17, 1983

[51] Int. Cl.[4] .......................... C07K 3/12; A23L 1/28; C12N 1/16

[52] U.S. Cl. ...................................... 435/272; 426/60; 435/69; 435/222; 435/255; 435/256; 435/267; 435/938

[58] Field of Search ..................... 426/60; 435/69, 222, 435/255, 256, 267, 272, 938

[56] References Cited

U.S. PATENT DOCUMENTS

| | | | |
|---|---|---|---|
| 2,364,008 | 11/1944 | Stuart | 99/14 |
| 3,036,918 | 5/1962 | Wingerd et al. | 99/20 |
| 3,212,902 | 10/1965 | Bavissotto | 99/9 |
| 3,459,637 | 8/1969 | Laufer et al. | 195/28 |
| 3,578,461 | 5/1971 | Weeks et al. | 99/7 |
| 3,733,207 | 5/1973 | McCabe | 99/17 |
| 3,736,147 | 5/1973 | Iacobucci et al. | 99/17 |
| 3,761,353 | 9/1973 | Noe et al. | 195/29 |
| 3,809,776 | 5/1974 | Chao | 426/431 |
| 3,830,942 | 8/1974 | Hawley | 426/190 |
| 3,857,966 | 12/1974 | Feldman et al. | 426/32 |
| 3,867,255 | 2/1975 | Newell et al. | 195/5 |
| 3,876,806 | 4/1975 | Hempenius et al. | 426/44 |
| 3,958,015 | 5/1976 | Gay | 426/18 |
| 3,960,659 | 6/1976 | Fazakerley | 195/5 |
| 3,970,520 | 7/1976 | Feldman et al. | 195/29 |
| 3,974,294 | 8/1976 | Schwille et al. | 426/32 |
| 3,989,592 | 11/1976 | Leavitt | 195/29 |
| 3,996,104 | 12/1976 | Lindblom et al. | 435/272 X |
| 3,997,397 | 12/1976 | Craveri et al. | 435/272 X |
| 4,007,088 | 2/1977 | Fenci et al. | 435/938 X |
| 4,107,334 | 8/1978 | Jolly | 426/7 |
| 4,341,802 | 7/1982 | Hopkins | 426/60 |

OTHER PUBLICATIONS

Viikari et al., "Reduction of Nucleic Acid Content of SCP", Process Biochemistry, May 1977, pp. 17–19 and 35.

Primary Examiner—David M. Naff

[57] ABSTRACT

Functional protein having reduced nucleic acid content is produced without initial denaturation of the protein by contacting undenatured yeast cells with an alkaline protease at a temperature of about 20° C. to 40° C. for about 2 minutes to 2 hours at a pH of about 8 to 11. The yeast cells are preferably *Pichia pastoris* and the alkaline protease is preferably from *Bacillus lichenformis*.

7 Claims, No Drawings

TREATMENT OF YEAST CELLS WITH PROTEOLYTIC ENZYMES

This invention relates to the treatment of microbial cells with alkaline proteolytic enzymes to form soluble protein material having good functional properties and a low nucleic acid content.

The desirability of protein having good functional properties is known in the art. Good functional properties for proteins are important because they relate to the flavor, color, solubility, thermal stability, emulsifying, foaming, and texturizing characteristics of the protein. It is generally recognized that protein fractions which are soluble have better functional properties than insoluble fractions.

Furthermore, it is known that microbial cells or single cell protein contain certain quantities of nucleic acids. The propriety of using these microbial cells for food and feed purposes is limited by the presence of nucleic acids which may cause certain pathologic effects such as arthritis and urinary calculus.

The prior art such as U.S. Pat. No. 4,107,334 shows that previously heat-denatured protein may be subjected to enzyme/heat treatment in order to improve the solubility and hence functional properties of the protein. Denaturation of the protein, of course, also requires heat treatment to temperatures as typically high as 150° C. which is very energy intensive and may cause undesirable degradation or cross-linking of the protein. It thus would be highly desirable if in some instances it was possible to do away with the denaturation step and yet achieve some solubilization of the protein as well as a reduction of the nucleic acid content therein.

It is therefore an object of the present invention to provide a simple and improved process for preparing functional protein reduced in nucleic acid content.

Other aspects, objects, and advantages of the present invention are apparent from the specification and claims.

In accordance with the present invention I have discovered that by treating yeast cells with an alkaline protease at a temperature of from about 20° C. to about 40° C. for about 2 minutes to 2 hours that partial solubilization of protein content of the cells occurs resulting in a protein fraction of reduced nucleic acid content with good functional properties. This is accomplished even though the previous denaturation step known in the prior art has been completely eliminated.

In accordance with the present invention, yeast cells are utilized.

Suitable species of yeasts include species from the genera Candida, Hansenula, Neurospora, Rhodotorula, Torulopsis, Saccharomyces, Schizosaccharomyces, Pichia, Debaryomyces, Kluyveromyces, Lipomyces, Cryptococcus, nematospora, and Brettanomyces.

Examples of suitable species include:
Candida boidinii
Candida utilis
Candida robusta
Candida rugosa
Hansenula minuta
Hansenula californica
Hansenula silvicola
Hansenula wickerhamii
Hansenula glucozyma
Hansenula nonfermentans
Torulopsis candida
Torulopsis versatilis
Torulopsis molishiana
Torulopsis nitratophila
Pichia farinosa
Pichia membranaefaciens
Pichia pastoris
Candida mycoderma
Candida stellatoidea
Candida claussenii
Brettanomyces petrophilium
Hansenula saturnus
Hansenula mrakii
Hansenula polymorpha
Hansenula capsulata
Hansenula henricii
Hansenula philodendra
Torulopsis bolmii
Torulopsis glabrata
Torulopsis nemodendra
Torulopsis pinus
Pichia polymorpha
Pichia pinus
Pichia trehalophila
Rhodotorula rubra Presently preferred yeast are those from the genus Pichia, with *Pichia farinosa, Pichia membranaefaciens* and *Pichia pastoris* most preferred.

The above described microorganisms can be grown in a batch or continuous fermentation process in the presence of oxygen, a source of carbon and energy, and an assimilable source of nitrogen. Various types of fermentation processes known in the art can be utilized. For example, a foam-filled fermenter such as described in U.S. Pat. No. 3,982,998 can be used.

Oxygen can be supplied to the fermentation process in the form of air or oxygen enriched air. The source of nitrogen for the fermentation can be any organic or inorganic nitrogen-containing compound which is capable of releasing nitrogen in a form suitable for metabolic utilization by the growing organism. Suitable organic nitrogen compounds include, for example, proteins, amino acids, urea, and the like. Suitable inorganic nitrogen sources include ammonia, ammonium hydroxide, ammonium nitrate, and the like.

The sources of carbon used with the above microorganisms can be any carbohydrate or starch containing material. For example, glucose (the hydrolysis product of starch), sucrose containing sugars, or hydrolyzed sucrose can all be utilized in the present invention. Straight chain alcohols having from 1 to 16 carbon atoms per molecule are utilizable as a carbon feedstock. Preferably the alcohol has from 1 to 6 carbon atoms per molecule and more preferably the alcohol will be either ethanol or methanol and most preferably, methanol. Examples of suitable alcohols include methanol, ethanol, 1-propanol, 1-butanol, 1-octanol, 1-dodecanol, 1-hexadecanol, 2-propanol, 2-butanol, 2-hexanol, and the like. Mixtures of alcohols can also be employed if desired. Other oxygenated hydrocarbons such as ketones, aldehydes, acids, esters, and ethers are also suitable substrates and these usually have from 1 to 20 carbon atoms per molecule. Normal paraffins having from 1 to about 20 carbon atoms per molecule can also be used as substrates.

Sufficient water is maintained in the fermentation so as to provide for the particular requirements of the microorganism employed. Minerals, growth factors, vitamins, and the like generally are added in amounts which vary according to the particular requirement of the microorganism and are generally known to those skilled in the art or are readily determined by those so skilled.

The growth of the microorganism is sensitive to the operating temperature of the fermentor and each particular microorganism has an optimum temperature for growth. Exemplary fermentation temperatures are in the range of about 20° C. to about 60° C.

Fermentation pressures are generally within the range of about 0.1 to about 100 atmospheres (10.13 to 10,132 kPa), more usually about 1 to 30 atmospheres (101.3 to 3,039 kPa), and more preferably about 1 to about 5 atmospheres (101.3 to 506.5 kPa) since the higher pressures mean a greater level of dissolved oxygen in the aqueous medium and usually higher productivities.

Any alkaline protease known in the art is suitable in the present invention. They may be of either microbial, plant, or animal original. Preferred are alkaline proteases of bacterial origin such as those derived from Bacillus species. Particularly suitable are those alkaline proteases derived from *B. licheniformis*.

The particular alkaline protease used must be present in an amount sufficient to solubilize the yeast cell single cell protein to the maximum desirable yet feasible level. As concerns the level of proteolytic activity used in the present invention, the maximum level is determined in part by economics.

Generally the temperature range for microbial cell-/enzyme contact is from about 20° C. to about 40° C., preferably from about 35° C. to about 40° C. The exact temperature employed will vary with the specific type of alkaline protease used.

Generally the reaction time is from about 2 min. to about 2 hours, preferably from about 15 minutes to about 60 minutes.

The use of an alkaline protease indicates, of course, that the reaction is carried out in a basic medium. Preferably, though, the pH should be from about 8 to about 11 and most preferably about 9. The exact pH will vary with the specific type of alkaline protease and SCP substrate used in the present invention.

It is within the scope of the present invention to immobilize the particular protease used on the SCP substrate as is known in the art. In this manner, the enzymatic digestion of the SCP could be carried out on a continuous basis in a countercurrent process or immobilized bed.

The following examples illustrate the present invention.

EXAMPLE I

A series of experiments were conducted in order to determine the effect that Alcalase enzyme has on single cell protein (SCP) extracts obtained from *Pichia pastoris*. Alcalase is a microbial alkaline protease derived from *B. lichenformis* supplied by Novo Enzyme Corp., Mamaroneck, N.Y.

In each experiment, 10 ml of 10% *Pichia pastoris* yeast suspensions (packed cell volume/volume) was prepared, the resulting suspension was adjusted to pH 9 and 0.25 mL of Alcalase 0.6 L was added. The mixture was incubated for one hour at the temperature indicated in Table I below.

The resulting treated SCP samples were centrifuged to sediment the remaining solids, carefully drained of the supernatant and resuspended to their original volume in water. The resuspended solids were analyzed for protein content, nucleic acid content and dry measure (DM) weight.

The results of each experiment are listed below in Table I.

TABLE I

| Expt. | SCP Preparation | Incubation Temp. (°C.) | In Solids Fraction After Digestion and Centrifugation | | | Calculated mg NA in 1 g Solubilized Protein*** |
|---|---|---|---|---|---|---|
| | | | Protein Remaining, % | Nucleic Acid Remaining, % | DM Wt. (g/l) | |
| 1 (Control) | Fresh cell cream, no added enzyme | 4° | 100* | 100** | 66.6 | 0 |
| 2 (Control) | Fresh cell cream, no added enzyme | 40° | 82 | 100 | 60.8 | 0 |
| 3 (Control) | Fresh cell cream, no added enzyme | 65° | 74 | 71 | 55.8 | 120 |
| 4 (Invention) | Fresh cell cream + Alcalase Enzyme | 40° | 76 | 98 | 56.3 | 10 |
| 5 (Prior Art) | Fresh cell cream, heat denatured for 2 min. at 65° C., then cooled to 40° C. and Alcalase added | 40° | 35 | 91 | 38.4 | 15 |

*Control (Expt. 1) was 40.8 mg/ml protein
**Control (Expt. 1) was 4.5 mg/ml N.A.
***[4.5 (mg/ml)-solids N.A. concentration (mg/ml)]/[40.8 (mg/ml)-solids Protein concentration (mg/ml)]

The above data indicate that the inventive treatment (Exp. 4), which does not involve protein denaturation before incubation results, not only in partial solubilization of the protein content but also results in lesser amounts of nucleic solubilized than in experiments involving a previous protein denaturation step (Run 5). Thus, the data show the benefits of eliminating the previous protein denaturation step in the preparation of soluble, protein digest.

EXAMPLE II

Effect of pH of Incubation

Samples of fresh cell cream were treated as in Example I, experiment 4 except that the pH during proteolytic digestion was adjusted to different values. All incubations were done at 40° C. for a period of one hour.

The results are given below in Table II.

TABLE II

| Expt. | Incubation pH | In Solids Fraction After Digestion and Centrifugation* | |
|---|---|---|---|
| | | Protein Remaining, % | Nucleic Acid Remaining, % |
| 1 | 7 | 90 | 87 |
| 2 | 9 | 76 | 91 |

*Contents relative to control (Example I, Expt. 1).

The above results show that protein digestion using alkaline protease proceeds best at higher pH values.

Reasonable variations and modifications are possible in the scope of the foregoing disclosure and the appended claims.

I claim:

1. A process for the recovery of functional protein from undenatured yeast cells which comprises contacting said undenatured yeast cells with an alkaline protease at a temperature of from about 20° C. to about 40° C. for about 2 minutes to 2 hours and at a pH of from about 8 to about 11.

2. A process according to claim 1 wherein said yeast cells are from the genera Pichia.

3. A process according to claim 2 wherein said yeast cells are *Pichia pastoris*.

4. A process according to claim 1 wherein said alkaline protease is derived from the genera Bacillus.

5. A process according to claim 4 wherein said alkaline protease is derived from *Bacillus lichenformis*.

6. A process according to claim 1 carried out at a temperature of from about 35° C. to about 40° C.

7. A process according to claim 1 carried out at a pH of 9.

* * * * *